United States Patent
Kiesslich et al.

(10) Patent No.: US 8,530,713 B2
(45) Date of Patent: Sep. 10, 2013

(54) METHOD FOR THE DEHYDROAROMATISATION OF MIXTURES CONTAINING METHANE BY REGENERATING THE CORRESPONDING CATALYSTS THAT ARE DEVOID OF PRECIOUS METAL

(75) Inventors: Frank Kiesslich, Dietzenbach (DE); Joana Coelho Tsou, Heidelberg (DE); Alexander Schulz, Mueden (DE)

(73) Assignee: BASF SE, Ludwigshafen (DE)

( * ) Notice: Subject to any disclaimer, the term of this patent is extended or adjusted under 35 U.S.C. 154(b) by 353 days.

(21) Appl. No.: 12/937,144

(22) PCT Filed: Apr. 1, 2009

(86) PCT No.: PCT/EP2009/053887
§ 371 (c)(1),
(2), (4) Date: Nov. 23, 2010

(87) PCT Pub. No.: WO2009/124870
PCT Pub. Date: Oct. 15, 2009

(65) Prior Publication Data
US 2011/0060176 A1 Mar. 10, 2011

(30) Foreign Application Priority Data
Apr. 8, 2008 (EP) .................................. 08154196

(51) Int. Cl.
*C07C 2/76* (2006.01)
(52) U.S. Cl.
USPC .............. 585/418; 585/419; 585/904; 502/53
(58) Field of Classification Search
USPC ........................... 585/418, 419, 904; 502/53
See application file for complete search history.

(56) References Cited

U.S. PATENT DOCUMENTS

| | | |
|---|---|---|
| 2007/0249880 A1 | 10/2007 | Iaccino et al. |
| 2007/0293709 A1 | 12/2007 | Iaccino et al. |
| 2008/0293980 A1 | 11/2008 | Kiesslich et al. |

FOREIGN PATENT DOCUMENTS

| | | |
|---|---|---|
| WO | 2006 011568 | 2/2006 |
| WO | 2007 048853 | 5/2007 |

OTHER PUBLICATIONS

Honda. K., et al., "Methane dehydroaromatization over Mo/HZSM-5 in periodic $CH_4$-$H_2$ switching operation mode," Catalysis Communications, vol. 4, pp. 21-26, (2003) XP 002993029.
Li, S., et al., "The function of Cu(II) ions in the Mo/CuH-ZSM-5 catalyst for methane conversion under non-oxidative condition," Applied Catalysis A: General, vol. 187, pp. 199-206, (1999).
Dong, Q., et al., "Studies on Mo/HZSM-5 Complex Catalyst for Methane Aromatization," Journal of Natural Gas Chemistry, vol. 13, No. 1, pp. 36-40, (2004).
Wang, L., et al., "Activity and stability enhancement of Mo/HZSM-5-based catalyst for methane non-oxidative transformation to aromatics and $C_2$ hydrocarbons: Effect of additives and pretreatment conditions," Applied Catalysis A: General, vol. 152, pp. 173-182, (1997).
Zhang, Y., et al., "Influence of Pretreatment Conditions on Methane Aromatization Performance of Mo/HZSM-5 and Mo-Cu/HZSM-5 Catalysts," Journal of Natural Gas Chemistry, vol. 12, No. 2, pp. 145-149, (2003).
Xu, Y., et al., "Direct conversion of methane under nonoxidative conditions," Journal of Catalysis, vol. 216, pp. 386-395, (2003).
Qi, S., et al., "Methane aromatization using Mo-based catalysts prepared by microwave heating," Catalysis Today, vol. 98, pp. 639-645, (2004).
Weckhuysen, B.M., et al., "Conversion of Methane to Benzene over Transition Metal Ion ZSM-5 Zeolites," Journal of Catalysis, vol. 175, Article No. CA982010, pp. 338-346, (1998).
Ma, H., et al., "Efficient regeneration of Mo/HZSM-5 catalyst by using air with NO in methane dehydro-aromatization reaction," Applied Catalysis A: General, vol. 275, pp. 183-187, (2004).
Ma, D., et al., "Mo/HMCM-22 Catalysts for Methane Dehydroaromatization: A Multinuclear MAS NMR Study," J. Phys. Chem. B, vol. 105, No. 9, pp. 1786-1793, (Feb. 8, 2001).
International Search Report issued Jul. 28, 2009 in PCT/EP09/053887 filed Apr. 1, 2009.
U.S. Appl. No. 12/937,062, filed Oct. 8, 2010, Kiesslich, et al.
U.S. Appl. No. 12/993,956, filed Nov. 22, 2010, Kiesslich, et al.
International Preliminary Report on Patentabilityt issued Jul. 23, 2010 in PCT/EP09/053887 filed Apr. 1, 2009.
U.S. Appl. No. 13/393,837, filed Mar. 2, 2012, Schneider, et al.
U.S. Appl. No. 13/500,966, filed Apr. 9, 2012, Tsou, et al.
U.S. Appl. No. 13/202,427, filed Aug. 19, 2011, Coelho Tsou, et al.
U.S. Appl. No. 13/260,053, filed Sep. 23, 2011, Coelho Tsou, et al.
U.S. Appl. No. 13/256,536, filed Sep. 14, 2011, Tsou, et al.

*Primary Examiner* — Thuan D Dang
(74) *Attorney, Agent, or Firm* — Oblon, Spivak, McClelland, Maier & Neustadt, L.L.P.

(57) ABSTRACT

The present invention relates to a process for nonoxidative dehydroaromatization of aliphatic hydrocarbons by converting a reactant stream comprising aliphatic hydrocarbons in the presence of a catalyst which comprises at least one metallosilicate as a support, at least one element selected from the group of Mo, W and Re as an active component and at least one further transition metal which is not a noble metal as a dopant, wherein the catalyst is regenerated regularly with hydrogen under nonoxidative conditions. The further transition metal used is preferably Fe, Ni, Cu and Co.

17 Claims, No Drawings

METHOD FOR THE DEHYDROAROMATISATION OF MIXTURES CONTAINING METHANE BY REGENERATING THE CORRESPONDING CATALYSTS THAT ARE DEVOID OF PRECIOUS METAL

The present invention relates to a process for nonoxidative dehydroaromatization of aliphatic hydrocarbons by converting a reactant stream comprising aliphatic hydrocarbons in the presence of a catalyst which comprises at least one metallosilicate as a support, at least one element selected from the group of Mo, W and Re as an active component and at least one further transition metal which is not a noble metal as a dopant, wherein the catalyst is regenerated regularly with hydrogen under nonoxidative conditions. The further transition metal used is preferably Fe, Ni, Cu and Co.

Aromatic hydrocarbons such as benzene, toluene, ethylbenzene, styrene, xylene and naphthalene constitute important intermediates in the chemical industry, the demand for which is still rising. In general, they are obtained by catalytic reformation from naphtha, which is itself obtained from crude oil. Relatively recent studies show that global mineral oil stocks are limited as compared with natural gas stocks. Therefore, the preparation of aromatic hydrocarbons from reactants which can be obtained from natural gas has also become an alternative of economic interest. The main component of natural gas is typically methane.

One possible reaction route to obtaining aromatics from aliphatics is that of nonoxidative dehydroaromatization (DHAM). The reaction is effected under nonoxidative conditions, especially with exclusion of oxygen. In DHAM, a dehydrogenation and cyclization of the aliphatics to the corresponding aromatics takes place with release of hydrogen.

For the catalysis of the nonoxidative dehydroaromatization, H-ZSM-5-zeolites which are modified with molybdenum and doped with further elements have been found to be particularly suitable.

L. Wang et al. (Applied Catalysis A: General 152, (1997), pages 173 to 182) conducted the nonoxidative dehydroaromatization over molybdenum-containing H-ZSM-5 catalysts and studied the influence of different pretreatment methods and the doping of the catalysts with further metals. The methane conversions were between 3 and 5% at selectivities for benzene and toluene of up to 96%. Doping with lanthanum and vanadium did not exhibit any positive effect; doping with tungsten or zirconium was found to be advantageous.

Y. Zhang et al. (Journal of Natural Gas Chemistry 12, (2003), pages 145 to 149) studied the influence of the pretreatment of Mo/H-ZSM-5 which had been doped with copper and used undoped on the hydroaromatization of methane. The presence of copper enhanced the methane conversion significantly from 7.5 to 10.5% by weight with equal benzene selectivity.

Y. Xu et al. (Journal of Catalysis 216, (2003), pages 386 to 395) describe, in a review article, the problems which occur when molybdenum-containing H-ZSM-5 catalysts are used for the dehydroaromatization of methane. More particularly, the deactivation of the catalyst by coke deposits constitutes a great problem. Y. Xu et al. summarize some of the means described in the literature for improving the activity and stability of Mo/H-ZSM-5 catalysts, such as steam dealumination, dealumination by acidic solutions or silanization.

S. Qi and W. Yang (Catalysis Today 98, (2004), pages 639 to 645) report that the methane conversion and the benzene selectivity over an Mo/H-ZSM-5 zeolite catalyst can be increased by measures including addition of copper. For instance, the conversion of methane rises from 18 to 20% at benzene selectivities of up to about 95%. The doping additionally has a positive influence on the stability and the coking tendency of the catalyst.

S. Li et al. (Applied Catalysis A: General 187, (1999), pages 199 to 206) studied the nonoxidative dehydroaromatization of methane over copper-doped Mo/H-ZSM-5 catalysts in comparison to the undoped catalysts. Commercially available H-ZSM-5 zeolite was calcined and boiled in water, and an ion exchange was carried out with ammonium nitrate. Subsequently, the zeolite was dried and calcined. In the case of the copper-doped zeolite, the copper ions were likewise applied by means of ion exchange. The zeolite pretreated in this way was subsequently mixed mechanically with the appropriate amount of molybdenum oxide and calcined. As a result of the doping of the catalyst with copper, the methane conversion rose from 7.4 to 10.1%, and the benzene selectivities rose from 92.7 to 94.8%. The decrease in the catalyst activity slowed owing to the doping with copper.

B. M. Weckhuysen et al., (Journal of Catalysis 175, (1998) pages 338 to 346) studied the conversion of methane to benzene in the presence of transition metal-doped H-ZSM-5 zeolites. For this study, different pretreatments were carried out on commercially available H-ZSM-5 catalysts. The zeolites were subjected to a partial or full ion exchange by means of aqueous solutions which comprised ammonium nitrate and sodium chloride in different concentrations in order to obtain zeolites which are present in the H form completely, only partly or not at all. The zeolites were subsequently doped with Ga, Zn or Cr in conjunction with Ru or Pt, and also Mo, Cu, Zn and Fe. Methane conversions of from 0.2 to 7.9% were found at benzene selectivities of 0 to nearly 80%.

Q. Dong et al. (Journal of Natural Gas Chemistry, 13 (2004), pages 36 to 40) are the authors of a comprehensive study of the influence of the doping of Mo/H-ZSM-5 with the transition metals Fe, Cr, Ga, Co, Ni, Zn, Ti, Rh, Re, Au and Ag. Relatively high methane conversions of from 10 to approx. 14% were obtained with a relatively large group of the dopants used, but the coking selectivity was significantly above 20% up to above 60% with the exception of Ga (14%).

The coke deposits referred to as coking have an unfavorable effect on the mass balance and the yield, since every molecule of reactant which is converted to coke is no longer available for the desired reaction to give aromatics. The coke selectivities achieved to date in the prior art are in most cases more than 20% based on the aliphatic converted.

Coking is additionally a great problem for the industrial employment of dehydroaromatization under nonoxidative conditions, since it lowers the activity of the catalyst within a relatively short time, which leads to short production cycles and a high regeneration demand. Frequently, coking is additionally associated with a shortened lifetime of the catalyst. The regeneration of the catalysts is not unproblematic either, since the starting activities firstly regularly have to be reestablishable for an economically viable process and this secondly has to be possible over a large number of cycles.

H. Ma et al. (Applied Catalysis, A: General 275 (2004), pages 183 to 187) describe the oxidative regeneration of an Mo/H-ZMS-5 used as a DHAM catalyst by means of air to which NO has been added. A fundamental disadvantage of the oxidative regeneration in the DHAM is that, in the case of inadequate purging with inert gas between the reaction phase in which the catalyst is laden with methane or other aliphatic hydrocarbons, and the regeneration phase in which oxidizing agents such as $O_2$ and NO are passed through the catalyst, explosive mixtures of methane and oxidizing agent can form. A purge step with inert gas between the two reaction phases is therefore always necessary and increases the level of complexity. In addition, the metallic elements present in oxidized form in the catalyst after the oxidative regeneration have to be converted back to the active form for reuse. A disadvantageous effect can be that many metal oxides are volatile at high temperatures.

According to D. Ma et al. (Journal of Physical Chemistry B 105 (2001), pages 1786 to 1793), the oxidative regeneration of Mo-laden H-MCM-22 and zeolites used as the catalyst in the DHAM causes a dealumination of the catalyst, which can eventually lead to major changes in the catalyst properties.

WO 2006/011568 describes a process for preparing aromatics and hydrogen by means of DHAM in the presence of Mo/H-ZSM-5 and Rh-doped Mo/H-ZSM-5. In this case, from 2 to 10% by weight of $H_2$ is added to the methane and the methane supply is interrupted completely for a certain time every few hours, in order to regenerate the catalyst in hydrogen atmosphere. The Rh-doped Mo/H-ZSM-5 catalyst approximates to the starting activity after regeneration to a significantly higher degree than the undoped catalyst. A disadvantage of this process is the use of the relatively expensive Rh as a dopant material.

The object of the present invention is an economically viable process for dehydroaromatization of aliphatic hydrocarbons, especially methane, to prepare aromatics such as benzene. This includes, more particularly, low costs for the catalyst, a high activity and stability of the catalyst, and a long lifetime. More particularly, a process shall be found in which the catalyst is regenerable repeatedly in a simple manner and without a high level of complexity, and the regular regeneration raises it back to the level of its starting activity or at least comes very close to this level.

The object is achieved in accordance with the invention by a process for nonoxidative dehydroaromatization of a reactant stream R comprising $C_1$-$C_4$-aliphatics, comprising the steps of I. converting the reactant stream R to a product stream in the presence of a catalyst which comprises
 a) at least one metallosilicate as a support,
 b) at least one element selected from the group of Mo, W and Re as an active component and
 c) at least one further transition metal which is not a noble metal as a dopant, and
II. regenerating the catalyst under nonoxidative conditions with a hydrogen-comprising mixture H.

Surprisingly, it is possible to regenerate a catalyst which comprises Mo, W and/or Re and is based on a metallosilicate support and whose activity has been reduced owing to coke deposits after it has been used in the DHAM, with complete or virtually complete attainment of the original catalyst activity, by means of hydrogen, when the catalyst is doped with at least one further element which is not a noble metal. The regeneration can be performed repeatedly with homogeneous or virtually homogeneous reattainment of the initial catalyst activity. The process according to the invention makes it possible to achieve long catalyst lifetimes with homogeneously high activity of the catalyst. The regeneration can be carried out with inert gas in a simple manner and without additional purge steps. At the same time, further activation steps are unnecessary.

According to the present invention, "nonoxidative" means, in relation to the DHAM, that the concentration of oxidizing agents such as oxygen or nitrogen oxides in the reactant stream R is below 5% by weight, preferably below 1% by weight, more preferably below 0.1% by weight. The mixture is most preferably free of oxygen. Likewise particularly preferred is a concentration of oxidizing agents in the mixture E which is equal to or lower than the concentration of oxidizing agents in the source for the $C_1$-$C_4$-aliphatics.

In relation to the regeneration, "nonoxidative" in the context of the present invention means that the coke deposits which originate from the DHAM on the catalyst, for the regeneration thereof, are not converted to CO and/or $CO_2$ by means of oxidizing agents. More particularly, the concentration of oxidizing agents such as oxygen or nitrogen oxides in the mixture H for use for regeneration in step II is below 5% by weight, preferably below 1% by weight, more preferably below 0.1% by weight.

As the support a), the catalyst comprises, in accordance with the invention, at least one metallosilicate. Preference is given to using aluminum silicates as the support a). Very particular preference is given to using, in accordance with the invention, zeolites as supports a). From the group of the zeolites, in accordance with the invention, preference is given to using zeolites of the pentasil type. Very particular preference is given to using zeolites with MFI structure and, among these, more preferably ZSM-5 zeolites; preference is likewise given to using zeolites of the MEL structure type and, among these, preferably ZSM-11, and zeolites of the MWW structure type; in this context, MCM-22 zeolite is particularly preferred. It is also possible to use mixtures of the different zeolites.

As well as Al, the zeolites may comprise further elements of the third main group, such as Ga, B or In.

Typically, the aforementioned zeolites are prepared by direct synthesis from alkali metal aluminate, alkali metal silicate and amorphous $SiO_2$ under hydrothermal conditions. In this context, organic template molecules, the temperature and further experimental parameters can be used to control the type of channel systems formed in the zeolite. In this synthesis, the zeolites are typically obtained in the sodium form. In the sodium form, the excess negative charge which is present in the crystal lattice owing to the exchange of 4-valent silicon atoms for 3-valent aluminum atoms is balanced out by sodium ions. Instead of sodium alone, the zeolite may also comprise further alkali metal and/or alkaline earth metal ions to balance the charge.

Preference is given to using the zeolites which are used with preference as supports a) in the H form, in which the zeolites are also commercially available. Very particular preference is given, as the support a), to an H-ZSM-5 zeolite with an $SiO_2$:$Al_2O_3$ ratio of from 10 to 100.

In the conversion from the Na form to the H form, the alkali metal and/or alkaline earth metal ions present in the zeolite are exchanged for protons. A customary process for converting the catalysts to the H form, which is preferred in accordance with the present invention, is a two-stage process in which the alkali metal ions and/or alkaline earth metal ions are first exchanged for ammonium ions. In the course of heating of the zeolites to from about 400 to 500° C., the ammonium ion decomposes to volatile ammonia and to the proton remaining in the zeolite. To this end, the zeolite is treated with an $NH_4$-containing mixture. The $NH_4$-containing component used in the $NH_4$-containing mixture is an ammonium salt selected from the group of ammonium halides, ammonium acetate, ammonium carbonate, ammonium hydrogencarbonate, ammonium nitrate, ammonium phosphate, ammonium hydrogenphosphate, ammonium dihydrogenphosphate, ammonium sulfate and ammonium hydrogensulfate. Preference is given to using ammonium nitrate as the $NH_4$-containing component.

The zeolite is treated with the $NH_4$-containing mixture by the known methods suitable for ammonium exchange of zeolites. These include, for example, impregnation, dipping or spraying the zeolite with an ammonium salt solution, the solution generally being employed in excess. The solvents used are preferably water or alcohols. The mixture comprises typically from 1 to 20% by weight of the $NH_4$ component used. The treatment with the $NH_4$-containing mixture is carried out typically over a period of several hours and at elevated temperatures. After the action of the $NH_4$-containing mixture on the zeolite, excess mixture can be removed and the zeolite washed. Subsequently, the zeolite is dried at from 40 to 150° C. for several hours, typically from 4 to 20 hours. This is followed by the calcination of the zeolite at temperatures of from 300 to 700° C., preferably from 350 to 650° C. and more preferably from 500 to 600° C. The duration of the calcination is typically from 2 to 24 hours, preferably from 3 to 10 hours, more preferably from 4 to 6 hours.

In a preferred embodiment of the present invention, the supports a) used are zeolites which have been treated at least twice with an $NH_4$-containing mixture and the supports a) have been dried and calcined between the first and second treatment. The at least two treatments with $NH_4$-containing mixtures and the drying and calcination are effected according to the above description.

Commercially available zeolites in the H form have typically already passed through a first ammonium exchange by treatment with an $NH_4$-containing mixture with subsequent drying and calcination. Therefore, commercially purchased zeolites present in the H form can be used in accordance with the invention as supports a), but preference is given to subjecting them to another treatment with an $NH_4$-containing mixture and if appropriate calcining before application of components b) and c).

The catalysts for use for the process according to the invention comprise at least one element selected from Mo, W and Re as the active component b). According to the invention, this is applied to the support a) by wet chemical or dry chemical means.

In wet chemical methods, Mo, W and Re are applied in the form of aqueous, organic or organic-aqueous solutions of their salts or complexes by impregnating the support with the appropriate solution. The solvent used may also be supercritical $CO_2$. The impregnation can be effected by the incipient wetness method, in which the porous volume of the support is filled by about the same volume of impregnation solution and—if appropriate after maturation—the support is dried. It is also possible to work with an excess of solution, in which case the volume of this solution is greater than the porous volume of the support. In this case, the support is mixed with the impregnation solution and stirred for a sufficiently long period. In addition, it is possible to spray the support with a solution of the appropriate metal compound. Other preparation methods known to those skilled in the art are also possible, such as precipitation of Mo, W and/or Re compounds on the support, spraying of a solution comprising Mo, W and/or Re compounds, sole impregnation, etc. Particularly suitable Mo, W or Re compounds are $(NH_4)_6Mo_7O_{24}$, $MoO_2$, $MoO_3$, $H_2MoO_4$, $Na_2MoO_4$, $(NH_3)_3Mo(CO)_3$, $Mo(CO)_6$. Particularly suitable W compounds are $(NH_4)_6W_{12}O_{39}$, $WO_2$, $WO_3$, $W(CO)_6$. Particularly suitable Re compounds are $NH_4ReO_4$, $ReO_2$, $ReO_3$, $Re_2(CO)_{10}$. After the active component b) has been applied to the support a), the catalyst is dried under reduced pressure or under air at from about 80 to 130° C., typically for from 4 to 20 hours.

According to the invention, the active component b) can also be applied by a dry chemical route, for example by depositing the metal carbonyls which are gaseous at relatively high temperatures, such as $Mo(CO)_6$, $W(CO)_6$ and $Re_2(CO)_{10}$, from the gas phase on the support. The deposition of the metal carbonyl compound is carried out after the calcination of the support.

According to the invention, the catalyst comprises from 0.1 to 20% by weight, preferably from 0.2 to 15% by weight, more preferably from 0.5 to 10% by weight, based in each case on the total weight of the catalyst, of the active component b). The catalyst may comprise only one element selected from Mo, W and Re; it may also comprise a mixture of two or else all three elements. The elements can be applied by wet chemical means together in one solution or in different solutions in succession with drying steps between the individual applications. The elements can also be applied mixed, i.e. one portion by wet chemical means and another portion by dry chemical means. Preference is given to using Mo as the active component b).

According to the present invention, the catalyst comprises at least one further transition metal which is not a noble metal as the dopant c). In the context of the present invention, noble metals are understood to mean the group consisting of Rh, Pd, Ag, Ir, Pt and Au. According to the present invention, preference is given to using Fe, Ni, Co and Cu and mixtures thereof as the dopant c).

To impregnate the support a) with the dopant c), the processes described above for the wet chemical impregnation of the support with the active component b) are employed. It is possible to use the customary metal compounds known to those skilled in the art. Particular preference is given to the nitrates, but it is also possible to use other salts known to those skilled in the art for wet chemical application. Suitable examples are halides, especially chloride, acetate, alkaline carbonates, formate, tartrate, acetate, complexes with ligands such as acetylacetonate, amino alcohols, EDTA, carboxylates such as oxalate and citrate, and hydroxycarboxylic acid salts.

When the active component b) is applied by wet chemical means, the dopant c) can be applied together with it. However, it is also possible to apply the dopant c) and the active component b) in succession, in which case each application is followed by drying. It may also be advantageous to maintain a certain sequence in the application. When the catalyst comprises more than one element as the dopant c), the active component b) and the elements used as the dopant may likewise be applied together or else successively, in which case the support is dried in each case between the different applications. In this case too, it may be advantageous to apply the individual elements of the dopant c) and the active component b) in a certain sequence.

In a preferred embodiment of the invention, the solution with which the active component b) and the dopant c) are applied to the zeolite comprises at least one complexing agent. The complexing agent is preferably selected from the group of acetylacetonate, amino alcohols, EDTA, carboxylates such as oxalate and citrate, and hydroxycarboxylic acid salts. Particular preference is given to using EDTA.

When the active component b) is applied by a dry chemical route, calcination is typically effected once again between the impregnation with the dopant c) and the dry chemical application of the active component b). If more than one further element is applied, these elements can be applied together or else in succession, in which case drying is effected between the individual impregnation stages. It may be advantageous to apply the individual elements in a certain sequence.

According to the invention, the dopant c) is present in the catalyst in a concentration of at least 0.1% by weight, based on the total weight of the catalyst. The inventive catalysts more preferably comprise at least 0.2% by weight, more preferably at least 0.5% by weight, of at least one further transition metal which is not a noble metal, based on the total weight of the catalyst.

Especially preferred in accordance with the invention are catalysts which comprise from 0.1 to 20% by weight of molybdenum and at least 0.1% by weight of Cu, based on the total weight of the catalyst. Very particular preference is given to catalysts which comprise 6% by weight of Mo and 1% by weight of Cu.

Also preferred in accordance with the invention are catalysts which comprise from 0.1 to 20% by weight of Mo and at least 0.1% by weight of Ni. Very particular preference is given to catalysts which comprise 6% by weight of Mo and 1% by weight of Ni.

In a further preferred embodiment of the present invention, the catalyst is mixed with an Si-containing binder. Suitable Si-containing binders are especially tetraalkoxysilanes, polysiloxanes and colloidal $SiO_2$ sols.

According to the invention, addition of the Si-containing binder is followed by a shaping step in which the catalyst material is processed by processes known to those skilled in the art to give shaped bodies. Shaping processes include, for example, spraying of a suspension comprising the support a) or the catalyst material, tableting, pressing in the moist or dry state, and extrusion. Two or more of these processes can also be combined. For the shaping, it is possible to use assistants such as pore formers and pasting agents, or else other additives known to those skilled in the art. Possible pasting agents are those compounds which lead to improvement in the mixing, kneading and flow properties. In the context of the present invention, these are preferably organic, especially hydrophilic, polymers, for example cellulose, cellulose derivatives such as methylcellulose, starch such as potato starch, wallpaper paste, acrylates, polyacrylates, polymethacrylates, polyvinyl alcohols, polyvinylpyrrolidone, polyisobutylene, polytetrahydrofuran, polyglycol ether, fatty acid compounds, wax emulsions, water or mixtures of two or more of these compounds. In the context of the present invention, pore formers include, for example, compounds which are dispersible, suspendable or emulsifiable in water or aqueous solvent mixtures, such as polyalkylene oxides, polystyrene, polyacrylates, polymethacrylates, polyolefins, polyamides, polyesters, carbohydrates, cellulose, cellulose derivatives, for example methylcellulose, natural sugar fibers, pulp, graphite or mixtures of two or more of these compounds. Pore formers and/or pasting agents are preferably removed from the resulting shaped body by at least one suitable drying and/or calcination step after the shaping. The conditions required for this purpose can be selected analogously to the parameters described above for calcination and are known to those skilled in the art.

The geometry of the catalysts obtainable in accordance with the invention may, for example, be spherical (hollow or solid), cylindrical (hollow or solid), annular, saddle-shaped, star-shaped, honeycomb-shaped or tablet-shaped. In addition, extrudates are useful, for example in strand form, trilobal form, quatralobal form, star form or hollow cylindrical form. In addition, the catalyst material to be shaped can be extruded and calcined, and the extrudates thus obtained can be crushed and processed to spall. The spall can be separated into different screen fractions. A preferred screen fraction has the particle size from 0.25 to 0.5 mm.

In a preferred embodiment of the invention, the catalyst is used in the form of shaped bodies or spall.

In a further preferred embodiment, the catalyst is used in the form of powder. The catalyst powder may comprise Si-containing binder, but may also be present free of si-containing binder.

When the inventive catalyst comprises an Si-containing binder, it is present in a concentration of from 5 to 60% by weight, based on the total weight of the catalyst, preferably from 10 to 40% by weight, more preferably from 15 to 30% by weight.

It may be advantageous to activate the catalysts used for dehydroaromatization of $C_1$-$C_4$-aliphatics before the actual reaction.

This activation can be effected with a $C_1$-$C_4$-alkane, for example ethane, propane, butane or a mixture thereof, preferably butane. The activation is carried out at a temperature of from 250 to 650° C., preferably at from 350 to 550° C., and a pressure of from 0.5 to 5 bar, preferably from 0.5 to 2 bar. Typically, the GHSV (gas hourly space velocity) in the activation is from 100 to 4000 $h^{-1}$, preferably from 500 to 2000 $h^{-1}$.

However, it is also possible to carry out an activation by virtue of the reactant stream R already comprising the $C_1$-$C_4$-alkane, or a mixture thereof, per se, or by adding the $C_1$-$C_4$-alkane, or a mixture thereof, to the reactant stream R. The activation is carried out at a temperature of from 250 to 650° C., preferably at from 350 to 550° C., and a pressure of from 0.5 to 5 bar, preferably from 0.5 to 2 bar. Typically, the GHSV (gas hourly space velocity) in the activation is from 100 to 4000 $h^{-1}$, preferably from 500 to 2000 $h^{-1}$.

In a further embodiment, it is also additionally possible to add hydrogen to the $C_1$-$C_4$-alkane.

In a preferred embodiment of the present invention, the catalyst is activated with an $H_2$-comprising gas stream, a $CH_4$-comprising gas stream or a $CH_4$- and $H_2$-comprising gas stream, in which case the gas stream used for the activation may additionally comprise inert gases such as $N_2$, He, Ne and/or Ar.

According to the invention, the reactant stream R comprises at least one aliphatic having from 1 to 4 carbon atoms. The aliphatics include methane, ethane, propane, n-butane, i-butane, ethene, propene, 1- and 2-butene and isobutene. In one embodiment of the invention, the reactant stream R comprises at least 50 mol %, preferably at least 60 mol %, more preferably at least 70 mol %, exceptionally preferably at least 80 mol %, especially at least 90 mol %, of $C_1$-$C_4$-aliphatics.

Among the aliphatics, particular preference is given to using the saturated alkanes. In that case, reactant stream R comprises preferably at least 50 mol %, preferably at least 60 mol %, more preferably at least 70 mol %, exceptionally preferably at least 80 mol %, especially preferably at least 90 mol %, of alkanes having from 1 to 4 carbon atoms.

Among the alkanes, methane and ethane are preferred, especially methane. In this embodiment of the present invention, the reactant stream R comprises preferably at least 50 mol %, preferably at least 60 mol %, more preferably at least 70 mol %, exceptionally preferably at least 80 mol %, especially at least 90 mol %, of methane.

The source used for the $C_1$-$C_4$-aliphatics is preferably natural gas. The typical composition of natural gas is as follows: 75 to 99 mol % of methane, 0.01 to 15 mol % of ethane, 0.01 to 10 mol % of propane, up to 6 mol % of butane and higher hydrocarbons, up to 30 mol % of carbon dioxide, up to 30 mol % of hydrogen sulfide, up to 15 mol % of nitrogen and up to 5 mol % of helium. Before use in the process according to the invention, the natural gas can be purified and enriched by methods known to those skilled in the art. The purification includes, for example, the removal of any hydrogen sulfide or carbon dioxide present in the natural gas and of further compounds which are undesired in the subsequent process.

The $C_1$-$C_4$-aliphatics present in the reactant stream R may also stem from other sources, for example may have originated in the course of crude oil refining. The $C_1$-$C_4$-aliphatics may also have been produced by renewable means (e.g. biogas) or synthetic means (e.g. Fischer-Tropsch synthesis).

If the $C_1$-$C_4$-aliphatic source used is biogas, the reactant stream R may additionally also comprise ammonia, traces of lower alcohols and further additives typical of biogas.

In a further embodiment of the process according to the invention, the reactant stream R used may be LPG (liquid petroleum gas). In a further embodiment of the process according to the invention, the reactant stream R used may be LNG (liquefied natural gas).

It is additionally possible to add hydrogen, steam, carbon monoxide, carbon dioxide, nitrogen and one or more noble gases to the reactant stream R.

According to the invention, the dehydroaromatization of $C_1$-$C_4$-aliphatics is carried out in the presence of the above-described catalysts at temperatures of from 400 to 1000° C., preferably from 500 to 900° C., more preferably from 600 to 800° C., especially from 650 to 750° C., at a pressure of from 0.5 to 100 bar, preferably at from 1 to 50 bar, more preferably at from 1 to 30 bar, especially from 1 to 10 bar. According to the present invention, the reaction is carried out at a GHSV (gas hourly space velocity) of from 100 to 10 000 $h^{-1}$, preferably from 200 to 3 000 $h^{-1}$.

The dehydroaromatization of $C_1$-$C_4$-aliphatics can in principle be carried out in all reactor types known from the prior art. A suitable reactor form is the fixed bed reactor, tubular reactor or tube bundle reactor. In these reactors, the catalyst is present as a fixed bed in one reaction tube or in a bundle of reaction tubes. The catalysts may likewise be used in the form of a fluidized bed or a moving bed in the corresponding reactor types suitable for this purpose, and the process according to the invention for dehydroaromatization can be carried out with the catalysts present in such a form.

According to the invention, the $C_1$-$C_4$-aliphatics are converted to aromatics with release of $H_2$. The product stream P therefore comprises at least one aromatic hydrocarbon selected from the group of benzene, toluene, ethylbenzene, styrene, xylene and naphthalene. It more preferably comprises benzene and toluene. The product stream further comprises unconverted $C_1$-$C_4$-aliphatics, hydrogen formed and the inert gases present in the reactant stream R, such as $N_2$, He, Ne, Ar, substances added to the reactant stream R such as $H_2$, and impurities already present in R.

In stage II of the process according to the invention, the catalyst is regenerated with a hydrogen-comprising mixture H under nonoxidative conditions. The mixture H comprises at least 50% by volume of $H_2$, preferably at least 80% by volume of $H_2$, more preferably at least 98% by volume of $H_2$.

The mixture H may additionally comprise inert gases such as the noble gases He, Ne and Ar and $N_2$.

The regeneration in stage II is carried out for at least 30 minutes, preferably at least 3 hours, more preferably at least 5 hours.

According to the present invention, the regeneration in stage II is carried out at least every 50 hours, preferably at least every 20 hours, more preferably at least every 6 hours of run time of stage I, i.e. the regeneration according to stage II is carried out after a reaction time of at most 50 hours, preferably at most 20 hours, more preferably at most 6 hours. The temperature in the regeneration according to stage II is at least 600° C., preferably from 700 to 850° C. According to the invention, the regeneration according to stage II is carried out at pressures of from 1 to 10 bar, preferably from 2 to 7 bar.

Between the reaction according to stage I and the regeneration according to stage II of the process according to the invention, the catalyst can be purged with an inert gas, for example He, Ar or $N_2$.

The present invention will be illustrated in detail hereinafter with reference to working examples. A to D illustrate the general methods.

A Treatment of a Zeolite with an $NH_4$-Containing Mixture 100 g of a commercially available zeolite in H form are mixed with 100 g of ammonium nitrate and 900 g of water, and heated at 80° C. in a stirred apparatus for 2 hours. After cooling, the suspension is filtered and washed with water. The filtercake is dried at 120° C. overnight.

B Mixing of the Zeolite with an Si-Containing Binder and Shaping 100 g of a zeolite are mixed with 10 g of sodium carboxymethylcellulose and, after adding 30 g of an Si-containing binder (Silres® MSE 100, Wacker Silicones), kneaded with addition of approx. 100 ml of water in portions for 60 minutes. The material thus obtained is extruded through a die with round cross section (diameter 2 mm) and the resulting extrudates are dried at 120° C. and calcined at 500° C. for 5 hours. The extrudates thus obtained are crushed and a screen fraction of from 0.25 to 0.5 mm is removed and is then correspondingly used further.

C Impregnation with Molybdenum 100 g of the zeolite support which may have been pretreated with $NH_4$ according to A and may have been converted to spall according to B are initially charged in a dish.

According to the target Mo content, an appropriate amount of ammonium heptamolybdate tetrahydrate (>98%, from ABCR) is made up with water to the appropriate volume of water absorption (approx. 100 ml) of the support and stirred until complete dissolution. The solution is subsequently added to the zeolite with stirring and the material is mixed further at room temperature for 10 min. The material is subsequently heated to 120° C. in a drying cabinet and dried overnight and then calcined at 500° C. for 5 h.

D Catalytic Test with Hydrogen Activation/Metered Addition

Approx. 1.6 g of the catalyst are heated to 375° C. under a helium atmosphere in the reactor tube (internal diameter=4 mm). At this temperature, hydrogen is switched on (approx. 10% by volume of He in $H_2$) and the catalyst is kept at this temperature for 5 h before it is brought slowly to 575° C. At this temperature, it is kept at approx. 10% by volume in He in $H_2$ for another 2 h. Thereafter, methane is switched on (approx. 85% by volume of $CH_4$, approx. 10% by volume of He, approx. 5% by volume of $H_2$) at a GHSV of 500 $h^{-1}$, and the catalyst is brought to the reaction temperature of 700° C.

After approx. 6 h, the mixture is inertized with helium and the temperature is raised to 750° C. and the pressure to p(sat.)=5 bar. This is followed by regeneration with pure $H_2$ for 4 h, going back to 700° C. and 1 bar under helium and then starting a new reaction cycle (T=700° C., p(sat.)=1 bar, approx. 85% by volume of $CH_4$, approx. 10% by volume of He, approx. 5% by volume of $H_2$, GHSV=500 $h^{-1}$).

E 6% by Weight of Mo on H-ZSM-5

A commercial H-ZSM5 (ZEOcat PZ-2/50-H, from ZEOCHEM, $SiO_2$: $Al_2O_3$=approx. 50 mol/mol) support was pretreated according to A and then converted to spall according to B. The zeolite support thus pretreated was subsequently impregnated according to C with approx. 6% by weight of Mo.

F 6% by Weight of Mo/1% by Weight of Cu on H-ZSM-5 (Inventive)

A commercial H-ZSM5 (ZEOcat PZ-2/50-H, from ZEOCHEM, $SiO_2$: $Al_2O_3$=approx. 50 mol/mol) support is pretreated according to A and then converted to spall according to B. 30 g of the zeolite support thus pretreated are initially charged in a dish. Approx. 3.6 g of ammonium heptamolybdate tetrahydrate (>98%, from ABCR) and approx. 1.18 g of copper(II) nitrate 2.5-hydrate (>99%, from Riedel-de-Haën) are made up with water to the appropriate volume of water absorption (approx. 24 ml) of the support and stirred until complete dissolution. The solution is subsequently added to the zeolite with stirring and the material is mixed further at room temperature for 15 min. The material is subsequently heated to 120° C. in a drying cabinet, dried overnight and then calcined at 500° C. for 5 h.

G 6% by Weight of Mo/1% by Weight of Co on H-ZSM-5 (Inventive)

A commercial H-ZSM5 (ZEOcat PZ-2/50-H, from ZEOCHEM, $SiO_2$: $Al_2O_3$=approx. 50 mol/mol) support is pretreated according to A and then converted to spall according to B. The zeolite support thus pretreated is subsequently impregnated according to C with approx. 6% by weight of Mo.

15 g of the zeolite support thus pretreated are initially charged in a dish. Approx. 0.61 g of cobalt(II) nitrate hexahydrate (>99%, from Acros Organics) are made up with water to the appropriate volume of water absorption (approx. 15 ml) of the support and stirred until complete dissolution. The solution is subsequently added to the zeolite with stirring and the material is mixed further at room temperature for 15 min. The material is subsequently heated to 120° C. in a drying cabinet, dried overnight and then calcined at 500° C. for 5 h.

Analysis:

| | |
|---|---|
| Co | 1.1 g/100 g |
| Mo | 5.6 g/100 g |

H 3% by Weight of Mo/1% by Weight of Fe on H-ZSM-5 (Inventive)

A commercial H-ZSM5 (ZEOcat PZ-2/50-H, from ZEOCHEM, $SiO_2$: $Al_2O_3$=approx. 50 mol/mol) support is pretreated according to A and then converted to spall according to B. The zeolite support thus pretreated is subsequently impregnated according to C with approx. 3% by weight of Mo.

15 g of the zeolite support thus pretreated are initially charged in a dish. Approx. 1.1 g of iron(III) nitrate nonahydrate (>97%, from Riedel-de-Haën) are made up with water to the appropriate volume of water absorption (approx. 15 ml) of the support and stirred until complete dissolution. The solution is subsequently added to the zeolite with stirring and the material is mixed further at room temperature for 15 min. The material is subsequently heated to 120° C. in a drying cabinet, dried overnight and then calcined at 500° C. for 5 h.

The catalyst is tested according to D.

Analysis:

| | |
|---|---|
| Fe | 1.2 g/100 g |
| Mo | 2.8 g/100 g |

I 6% by Weight of Mo/1% by Weight of Ni on H-ZSM-5 (Inventive)

A commercial H-ZSM5 (ZEOcat PZ-2/50-H, from ZEOCHEM, $SiO_2$: $Al_2O_3$=approx. 50 mol/mol) support is pretreated according to A and then converted to spall according to B. 20 g of the zeolite support thus pretreated are initially charged in a dish. Approx. 2.3 g of ammonium heptamolybdate tetrahydrate (>98%, from ABCR) and approx. 1.06 g of nickel(II) nitrate hexahydrate, $Ni(NO_3)_2 \cdot 6H_2O$ (>99%, from Merck KGaA) are made up with water to the appropriate volume of water absorption (approx. 15 ml) of the support and stirred until complete dissolution. The solution is subsequently added to the zeolite with stirring and the material is mixed further at room temperature for 15 min. The material is subsequently heated to 120° C. in a drying cabinet, dried overnight and then calcined at 500° C. for 5 h.

The catalyst is tested according to D.

Analysis:

| | |
|---|---|
| Ni | 1.0 g/100 g |
| Mo | 5.8 g/100 g |

The comparison of the catalytic performance of the catalysts from examples E-I is shown in table 1. SOR is the abbreviation of "start of run", which denotes the starting activity, for example 1 h after the start of the cycle.

| Catalyst | Conversion, cycle 1, SOR after 1 h | Conversion, cycle 3, SOR after 1 h | Conversion, cycle 5, SOR after 1 h |
|---|---|---|---|
| Mo | 8.8 | 8.3 | 7.9 |
| Mo/Cu | 15.0 | 14.6 | 12.9 |
| Mo/Co | 16.3 | 15.8 | 13.4 |
| Mo/Fe | 14.7 | 11.9 | 11.6 |
| Mo/Ni | 10.5 | 10.3 | 10.2 |

Conversion: % of methane converted based on methane used

The invention claimed is:

1. A process for nonoxidative dehydroaromatization of a reactant stream R comprising $C_1$-$C_4$-alkanes to a product stream P, comprising $H_2$ and at least at least one aromatic hydrocarbon selected from the group of compounds consisting of benzene, toluene, ethylbenzene, sturene, xylene and naphthalene, the process comprising:
   I) converting the reactant stream R at a temperature of from 400 to 1000° C. and a pressure of from 0.5 to 100 bar in the presence of a catalyst which comprises:
      a) at least one metallosilicate as a support,
      b) at least one element selected from the group of Mo, W and Re as an active component and
      c) at least one further transition metal which is not a noble metal as a dopant, and when an activity of the catalyst is reduced,
   II) regenerating the catalyst under nonoxidative conditions with a hydrogen-comprising mixture H,
   wherein
   when the catalyst is prepared, prior to applying the at least one element b) and dopant c) to the support a) the metallosilicate support is treated at least twice with a mixture comprising $NH_4$ and the support a) is dried and calcined between the first and second treatment.

2. The process according to claim 1, wherein the at least one metallosilicate of the catalyst comprises an aluminosilicate.

3. The process according to claim 1, wherein the at least one metallosilicate of the catalyst comprises a zeolite.

4. The process according to claim 3, wherein the zeolite is selected from the group consisting of MFI, MWW and MEL.

5. The process according to claim 1, wherein the metallosilicate comprises an H-ZSM-5 with an $SiO_2$:$Al_2O_3$ ratio of from 10 to 100.

6. The process according to claim 1, wherein the support a) is treated more than twice with a mixture comprising $NH_4$ and the support a) is dried and calcined between the first and second treatment.

7. The process according to claim 1, wherein the active component b) comprises Mo.

8. The process according to claim 1, wherein the dopant c) comprises at least one transition metal selected from the group consisting of Co, Cu, Fe and Ni.

9. The process according to claim 1, wherein a content of the active component b) is from 0.1 to 20% by weight.

10. The process according to claim 1, wherein a content of the dopant c) is at least 0.1% by weight.

11. The process according to claim 1, wherein the application of the active component b) and the active component c) comprises applying a solution of components b) and c) and at least one complexing agent.

12. The process according to claim 1, wherein a content of $H_2$ in the mixture H is at least 50% by volume.

13. The process according to claim 1, wherein a time of the regeneration is at least 30 min.

14. The process according to claim 1, wherein the regeneration is conducted at a time interval of at least every 50 h of run time of the conversion.

15. The process according to claim 1, wherein a temperature of the regeneration is at least 600° C.

16. The process according to claim 1, wherein a pressure of the regeneration is from 1 to 20 bar.

17. The process according to claim 1, wherein the $C_1$-$C_4$-alkanes of reactant stream R comprises at least 50% by volume of methane.

* * * * *